United States Patent
Liu et al.

(10) Patent No.: US 9,603,362 B2
(45) Date of Patent: Mar. 28, 2017

(54) ORGANIC ACID ANTIMICROBIAL COMPOSITIONS

(71) Applicant: Solenis Technologies, L.P., Schaffhausen (CH)

(72) Inventors: Zhaoqing Liu, Pennington, NJ (US); Corinne E. Consalo, New Castle, DE (US); John S. Chapman, Lincoln University, PA (US)

(73) Assignee: Solenis Technologies, L.P. (CH)

( * ) Notice: Subject to any disclaimer, the term of this patent is extended or adjusted under 35 U.S.C. 154(b) by 0 days.

(21) Appl. No.: 14/657,680

(22) Filed: Mar. 13, 2015

(65) Prior Publication Data

US 2015/0257382 A1    Sep. 17, 2015

Related U.S. Application Data

(60) Provisional application No. 61/953,416, filed on Mar. 14, 2014.

(51) Int. Cl.
| | |
|---|---|
| *A01N 35/06* | (2006.01) |
| *A01N 37/36* | (2006.01) |
| *A01N 65/08* | (2009.01) |
| *A23L 3/3472* | (2006.01) |
| *A23L 3/3508* | (2006.01) |
| *A23L 3/3463* | (2006.01) |

(52) U.S. Cl.
CPC .............. *A01N 35/06* (2013.01); *A01N 37/36* (2013.01); *A01N 65/08* (2013.01); *A23L 3/3472* (2013.01); *A23L 3/34635* (2013.01); *A23L 3/3508* (2013.01)

(58) Field of Classification Search
CPC ........ A61K 8/068; A01N 35/06; A01N 37/36; A01N 65/08; A23L 3/34635; A23L 3/3472; A23L 3/3508
See application file for complete search history.

(56) References Cited

U.S. PATENT DOCUMENTS

| | | | |
|---|---|---|---|
| 5,283,056 A * | 2/1994 | Chung ................... | A61K 8/062 424/49 |
| 5,294,364 A | 3/1994 | Thomas et al. | |
| 5,968,539 A | 10/1999 | Beerse et al. | |
| 6,251,844 B1 | 6/2001 | Leonard et al. | |
| 6,451,365 B1 | 9/2002 | King et al. | |
| 6,475,537 B1 | 11/2002 | King et al. | |
| 7,030,070 B2 | 4/2006 | Sakurai et al. | |
| 7,354,888 B2 | 4/2008 | Mostoller | |
| 7,642,227 B2 | 1/2010 | Kurtz | |
| 7,851,430 B2 | 12/2010 | Kurtz | |
| 2002/0165130 A1 | 11/2002 | Johnson et al. | |
| 2002/0187914 A1 * | 12/2002 | Massaux ................... | C11D 1/72 510/417 |
| 2002/0197366 A1 | 12/2002 | King et al. | |
| 2004/0175480 A1 | 9/2004 | Seman et al. | |
| 2005/0048020 A1 * | 3/2005 | Wille ..................... | A61K 8/062 424/70.13 |
| 2006/0134024 A1 | 6/2006 | Trivedi et al. | |
| 2007/0258996 A1 * | 11/2007 | Mookerjee ............. | A01N 27/00 424/195.15 |
| 2009/0286884 A1 | 11/2009 | Ono et al. | |
| 2013/0012428 A1 * | 1/2013 | Jacobus ................ | A01N 43/72 514/2.4 |
| 2014/0072691 A1 * | 3/2014 | Scheller ................ | B01F 3/0807 426/600 |

FOREIGN PATENT DOCUMENTS

| | | | |
|---|---|---|---|
| WO | 0100777 | 1/2001 | |
| WO | 0164035 | 9/2001 | |
| WO | 2014143938 | 9/2014 | |
| WO | 2014152683 | 9/2014 | |
| WO | WO2014/014938 | * 9/2014 | ............. A01N 35/06 |

OTHER PUBLICATIONS

Ron Kotrba, Yeast Unbound, Ethanol Producer Magazine, Aug. 1, 2006, 3 pages (obtained online, www.ethanolproducer.com).*
Safety Data Sheet of LactoStab®, 4 pages, 2013.*
International Search Report, PCT/IB2015/000727, p. 1-3, Jul. 13, 2015.
Arunachalam Muthaiyan et al., Antimicrobial strategies for limiting bacterial contaminants in fuel bioethanol fermentations, Progress in Energy and Combustion Science, 37 (2011) 351-370.
B. Kramer, et al., Antimicrobial activity of hop extracts against foodborne pathogens for meat applications, Journal of Applied Microbiology, 118 (2014) 648-657.
L. Ruckle, et al., Hop acids can efficiently replace antibiotics in ethanol product, Universitat Hohenheim Institut for Food Technology, (1981) 139-147.

* cited by examiner

*Primary Examiner* — Karlheinz R Skowronek
*Assistant Examiner* — Joseph Fischer
(74) *Attorney, Agent, or Firm* — Joanne Rossi; Michael Herman

(57) ABSTRACT

An antimicrobial composition comprises at least one or more organic acid or salt in water, one or more antimicrobial agent which has limited water-solubility. The composition contains high active content and is stable for long period of time.

22 Claims, No Drawings

ORGANIC ACID ANTIMICROBIAL COMPOSITIONS

This application claims the priority of U.S. provisional application No. 61/953,416 filed Mar. 14, 2014, the contents of which is hereby incorporated by reference.

FIELD OF THE INVENTION

The present invention relates to a stable composition, consisting of GRAS substances, for microbial control, specifically in fermentation processes

BACKGROUND OF THE INVENTION

Organic carboxylic acids are generally known to have antimicrobial properties. Recent work has shown synergistic effect between organic carboxylic acids and other types of antimicrobial agent, such as hops acid. For example, US application 2004/0175480 described that the hops beta acids were more effective as antimicrobial agent if they were in combination with food grade acid, such as lactic acid, acetic acid, propionic acid, citric acid, a potassium ion source, and an antioxidant.

Antimicrobial organic acids are generally soluble in water at high concentration, but some of the organic acid antimicrobial agents are not soluble in water or salted out in the presence of electrolyte. As an example, hops acids are known to have limited solubility in water and the antimicrobial compositions of hops acids described in prior arts are low in active even with the use of organic solvents such as glycols or suspension agents.

One way to combine the different antimicrobial is to spray the liquid antimicrobial agent onto the powdery organic acid or salt, but the resulting composition is not easily dispersible in water. Although wetting or/and emulsifying agents can be formulated into the solid composition, it is more convenient to have liquid products with high active content for handling and use. Products with high active content also save cost in processing, transportation and storage from the sustainability point of view.

It is known that surfactant can help solubilize hydrophobic material in water. Surfactants such as those described in U.S. Pat. Nos. 5,374,614, 7,655,613 and 7,846,889 were utilized to form microemulsions, a thermodynamically stable isotropic liquid, from water-soluble and water-insoluble ingredients. Such microemulsion compositions containing organic acids were also described in U.S. Pat. Nos. 5,294,364, 6,251,844, 7,030,070 and 7,642,227 as acidic cleaning liquids. The organic acid content is low and surfactants used might be prohibited from applications in food or articles in contact with food.

It is desirable to have a single product with all synergistic antimicrobial components in a stable concentrated form with water as the solvent. It is much preferred that the antimicrobial product is of little concern in terms of flammability, corrosivity, toxicity and regulatory requirements.

DESCRIPTION OF THE INVENTION

The invention provides for an aqueous antimicrobial composition comprising: (i) water soluble organic acids or their salts, (ii) antimicrobial agents with limited water-solubility, and (iii) surfactants.

This invention provides a non-hazardous stable aqueous antimicrobial composition comprising water soluble organic acids and antimicrobial agents of limited water-solubility at high active content, preferably greater than 10%, more preferably greater than 20% and most preferably greater than 30% of the total weight of the composition. The compositions are formulated with GRAS (Generally Recognized as Safe) ingredients that are authorized to be used in food and beverage and the compositions are classified as none hazardous materials in terms of flammability and corrosively. The compositions are stable as homogeneous liquid for greater than 1 month, preferably greater 3 months and most preferably greater than 6 months at room temperature or below.

The compositions according to the present invention were designed to function as antimicrobial agents, preferably in reducing or controlling the concentration of undesirable micro-organisms in fermentation processes. Such similar compositions could also be used for other purposes such as for anti-parasites or as concentrating cleaning, de-scaling and disinfecting agents. The active components of the composition comprise one or more organic acids or their salts, and one or more antimicrobial agents of limited water solubility, with a total active content (organic acid plus antimicrobial agent) greater than 5% by weight, preferably greater than 15% and most preferably greater than 25% based on the total weight of the composition. The compositions also comprise one or more surfactant solubilizer. These include but not limited to anionic surfactants, non-ionic surfactants, amphoteric surfactants, zwitterionic surfactants and cationic surfactants. Additional ingredients such as neutralizing agent, solvent can also be added to increase the total active content without destabilizing the composition. Functional agents could also be added such as chelating agents, sequestrants, corrosion inhibitor, enzymes, surface modification agents, dyes and fragrances.

The water soluble organic acids preferred for use in the invention are selected from water-soluble organic mono- and polycarboxylic acids with two to eight carbon atoms in the molecule and optionally substituted by one or more hydroxy groups. Suitable classes are alkanoic acids, hydroxyalkanioc acids, alkyl polycarboxylic acids and hydroxyalkyl polycarboxylic acids. Preferred herein are mono- and polycarboxylic acids which have a pKa value, related to the first dissociation stage of less than about 6. These include, for example, acetic acid, adipic acid, benzenesulfonic acid, benzoic acid, citric acid, gluconic acid, glutaric acid, hydroxyacetic acid, lactic acid, malic acid, methanesulphonic acid, oxalic acid, propionic acid, salicylic acid, succinic acid, tartaric acid, and mixtures thereof as well as their salts. A preferred acid is citric acid or its salt. For purposes of this invention hops acids is not an organic acid.

The water soluble organic acid content is from 5 to 70%, from 5 to 60%, from 5 to 50%, preferably 15 to 60%, most preferably 25-50% by weight within the total composition.

Suitable antimicrobial agents of limited solubility include hops acids or nisin. The term "hops acids" as used herein includes hops beta acids, hops alpha acids, their isomerized or derivatized products and their salts. It also includes hops extracts such as those described in U.S. Pat. No. 5,286,506. The chemical identities of alpha and beta hops acids include cohumulones, humulones, adhumulones, colupulones, lupulones and adlupulones. These all are included in the term "hops acids" as use herein. Hops acids can be prepared by extraction and purification from natural hops or by chemical synthesis. A preferred antimicrobial agent is hops acids.

The hydrophobic antimicrobial component, preferably hops acids, active contents are from 0.05 to 15%, preferably 0.1 to 10%, most preferably 0.5-5% by weight within the total composition.

The surfactant solubilizing or emulsifying agents for antimicrobial components of low water-solubility include nonionic, anionic, cationic, amphoteric and zwitterionic surfactants. Surfactants described in U.S. Pat. Nos. 7,846,889, 7,030,070, 6,251,844 and 5,294,364 are herein incorporated by reference. Preferred surfactants are those authorized to be used as food and pharmaceutical ingredients or in articles with potential food contact. These surfactants include polysorbates (polyoxyethylene sorbitan fatty acid esters) such as the Tweens (Croda Inc), mono or dialkyl sulfosuccinates such as Aerosol OT (Cytec), alkyl polyglucosides such as Glucopons (BASF) and alkyl sulfates. Preferred surfactants for use in the invention include polyoxyethylene (20) sorbitan monooleate and alkyl polyglucosides.

The composition can contain one or more surfactants from one single group or from different groups of surfactants. The amount of one or more surfactants in the compositions is from 0.1 to 30%, preferably 1 to 20%, most preferably 2-15% by weight within the total composition.

A limited amount of organic solvent or co-surfactants can also be used so that the amount of surfactant can be reduced. Examples are fatty alcohols such as methanol, ethanol, propanol, butanol, glycols or polyhydric alcohol of ethylene glycol, propylene glycol, glycerol; fatty acids or diacids such as butanoic acid, adipic acid, octanoic acid. Preferred co-surfactants include ethanol, propylene glycol and adipic acid.

The composition may contain one or more co-surfactants or organic solvents from one single group or from different types. The amount of the one or more co-surfactants or organic solvents in the composition is from 0.1 to 30%, preferably 1 to 20%, most preferably 2-10% by weight within the composition.

The organic acid can be neutralized totally or partially with alkali or alkali earth hydroxide, ammonium hydroxide, or organic amines. Examples are sodium hydroxide, potassium hydroxide and ammonia. The degree of neutralization depends on the type and the amount of organic acids. Typically, the composition should be neutralized to pH above 2 to reduce the corrosiveness of the organic acid, but no more than pH 4 to retain the highest active content possible. However, for high stability of the composition, neutralization to alkaline pH is preferred.

The composition is preferred to be formulated as a micro-emulsion, a thermodynamically stable, isotropic liquid mixture of oil and water containing surfactant preferably with a co-surfactant or solvent. The organic acid is first dissolved in water and neutralized to the desired pH, and then mixed with at least one surfactant, at least one co-surfactant and at least one antimicrobial agent of limited water-solubility. It is preferred that the hydrophobic antimicrobial agent is first dissolved in at least one surfactant and at least one co-surfactant or at least one solvent to make a pre-blend, which is then diluted with neutralized organic acid aqueous solution.

It is preferred all components of the antimicrobial composition are authorized as food ingredients or granted GRAS (Generally Recognized as Safe) status by FDA. It is also preferred the composition is none hazardous in terms of corrosiveness and flammability.

The compositions provide a powerful, non-antibiotic, antimicrobial treatment. The composition can be used for reducing undesirable microorganism concentration, promoting desirable microorganism propagation, and increasing desirable microorganism efficiency in an aqueous system.

In the foregoing method, the "undesirable" microorganisms intended to be reduced are those that compete for nutrients with the desirable microorganisms that promote the desired fermentation processes. Unwanted or undesirable microbes in fermentation include the lactic acid producing bacteria (LAB) and the acetic acid producing bacteria of which *Lactobacillus* and *Acetobacter* are prominent representatives. Any microbe that competes for the fermentable substrate, denying it to the intended fermenting organism and thus reducing yields can be considered undesirable. In this regard, the hops acid extract and organic acid employed in the present method do not detrimentally affect the growth and viability of desirable, fermentation-promoting microorganisms, but does eliminate or suppress the growth of undesirable microorganisms that interfere with the fermentation process. Moreover, the elimination or suppression of undesirable microorganisms has a favorable effect on the growth and viability of desirable microorganisms.

The method of controlling undesirable microorganism concentration in an aqueous solution employed in a fermentation process comprising the steps of: introducing a fermentable carbohydrate to an aqueous solution, introducing at least one yeast to the aqueous solution, and introducing the composition containing (a) the water soluble organic acids or their salts, (b) the antimicrobial agents with limited water-solubility, and (c) the surfactants to the aqueous solution.

The composition is added to the fermentation system in order to control the undesirable microorganism concentration such that the amount of the organic acid in the fermentation system is from 12500 ppm down to 100 ppm, from 6250 down to 100 ppm, or from 4000 down to 100 ppm, or from 4000 down to 200 ppm. Generally at least 100 ppm or at least 200 ppm or at least 300 ppm of organic acid is used. The composition is added to the fermentation system such that the amount of the antimicrobial agent with limited water-solubility in the fermentation system is from 0.5 ppm to 200 ppm, or from 0.5 ppm to 150 ppm, or from 2 to 150 ppm, or from 2 to 100 ppm. Generally the amount of hops acid used in is at least 2 ppm or at least 5 ppm.

EXAMPLES

Example #1

Mixing Tween 80 (polyoxyethylene (20) sorbitan monooleate), 10.82 parts, absolute ethanol, 3.74 parts and hops acid, potassium salt (30% active acid), 3.15 parts in the order described to give a homogeneous liquid. In a separate vessel, dissolve citric acid, anhydrous 34.49 parts in demineralized water 34.49 part, and the cold solution was then neutralized by adding ammonium hydroxide of 28-30% ammonia content, 6.02 parts. The partially neutralized citric acid was then added to the organic phase containing hops acid, resulting in an isotropic liquid of about 35% active combined antimicrobial agents. The composition was found stable at 4° C. without crystallization of citrate salt and stayed as homogeneous for 1 month at 50° C. No negative effect was observed as an antimicrobial agent with the formulation.

TABLE 1

Compositions of Citric and Hops Acid (percent by weight)

| | Example # 1 | Example # 2 |
|---|---|---|
| Citric Acid, anhydrous | 34.49 | 37.84 |
| D. Water | 41.78 | 45.84 |
| Ethanol, 99.5%, absolute | 3.74 | 2.05 |
| Tween 80 | 10.82 | 5.94 |
| Ammonium hydroxide, 28-30% NH3 | 6.02 | 6.60 |
| HOPS Acid, 30% | 3.15 | 1.73 |
| Stability: | | |
| F/T (−20° C.) | Stable as liquid | Stable as liquid |
| 4° C. (crystallization) | >46 days | >46 days |
| 22° C. | >76 days | >76 days |
| 32° C. | >70 days | >70 days |
| 50° C. (liquid phase separation) | 30 days | 37 days |

Example #2

The same procedure as in Example #1 was applied with the charges listed in Table 1 to yield a composition of 38% active combined active antimicrobial agents. The composition was found stable for at 4° C. and room temperature without crystallization of citrate salt and stayed as homogeneous for 37 days at 50° C. (Table 1). Again, no adverse effects were observed in antimicrobial properties with the formulation.

Examples #3 to 11

Three GRAS status surfactants, that is, Tween 80, Aerosol OT-70PG (Cytec), and alkyl polyglucoside of Triton BG-10 (Dow) or Glucopon 215 UP (BASF), were formulated in these Examples according to charges listed in Table 2. Citric acid was first dissolved in water and then partially neutralized with ammonia. The surfactants, Tween 80, Aerosol OT-70PG, Triton BG-10 or Glucopon 215 UP were added as listed, followed by hops acids and ethanol. After thorough mixing, a homogeneous liquid was always obtained with shelf life listed in Table 2.

Examples 12-13

In these examples potassium hydroxide was used as neutralizing agent. The same procedure as Examples #3-10 was followed with charges by weight listed in Table 3. The active contents of antimicrobial agents were increased to above 40%, but the shelf life was limited. The instability was thought to be caused by the acid-liable surfactant solubilizers.

Examples 14-16

In these examples potassium hydroxide was used to neutralize the acids toward alkaline pH for high stability. Alternative co-surfactants of non-flammable propylene and/or adipic acid were also used as shown in Table 4 of these compositions. The same procedure as Examples #3-10 was followed with charges by weight listed in Table 4. No hydrolysis of the surfactants used was expected, and no destabilization and little discoloration of hops acid were observed upon aging for more than 6 weeks at 4, 22 and 50° C.

TABLE 3

Compositions of Citric and Hops Acid (percent by weight)

| | Example # 12 | Example # 13 |
|---|---|---|
| D. Water | 39.47 | 41.96 |
| Aerosol OT-75 (in ethanol) | 3.78 | 2.87 |
| Tween 80 | 5.27 | 2.81 |
| Citric acid, anhydrous | 39.39 | 41.47 |
| 45% KOH | 8.50 | 9.00 |
| 30% Isoalpha Acid, Extract | 3.59 | 1.89 |
| Stability: | | |
| F/T (−20° C.) | Stay as liquid | Stay as liquid |
| 4° C. | >2 month | >2 month |
| 22° C. | 10 weeks | 4 weeks |
| 50° C. | <24 hr | <24 hr |

TABLE 2

Compositions of Citric and Hops Acid (percent by weight)

| Example # | 3 | 4 | 5 | 6 | 7 | 8 | 9 | 10 | 11 |
|---|---|---|---|---|---|---|---|---|---|
| Citric Acid, anhydrous | 34.49 | 33.77 | 32.33 | 33.37 | 34.18 | 33.56 | 33.35 | 34.49 | 32.03 |
| D. Water | 41.78 | 40.90 | 39.15 | 40.41 | 41.38 | 40.64 | 40.40 | 41.78 | 38.99 |
| Ethanol, 99.5%, absolute | 4.15 | 4.19 | 3.86 | 3.98 | 4.13 | 4.07 | 4.16 | 4.30 | 3.34 |
| Tween 80 | | | | 11.62 | 10.16 | 2.72 | | 10.25 | 11.82 |
| Aerosol OT-70PG | 4.94 | 1.48 | 10.86 | 1.75 | | | 1.47 | | |
| Triton BG-10 | 5.48 | 10.68 | 5.20 | | 1.08 | 10.01 | | | |
| Glucopon 215 UP | | | | | | | 11.70 | | 4.57 |
| Aq. NH3, 28-30% | 6.02 | 5.90 | 5.65 | 5.83 | 5.97 | 5.86 | 5.83 | 6.02 | 5.62 |
| HOPS Acid, 30% | 3.14 | 3.08 | 2.96 | 3.04 | 3.11 | 3.14 | 3.10 | 3.16 | 3.63 |
| Stability: | | | | | | | | | |
| F/T (−20° C.) | liquid | liquid | liquid | liquid | liquid | liquid | stable | stable | stable |
| 4° C. (crystallization), days | >43 | >70 | >43 | >70 | >70 | >70 | >56 | >56 | >36 |
| 22° C., days | 20 d | >70 d | 20 d | >70 d | >70 d | >70 d | >56 d | >56 d | >36 |
| 50° C. (phase separation), days | 2 | 36 | 2 | 54 | 70 | 30 | 34 | 56 | >36 |

TABLE 4

Alkaline Compositions of
Citric and Hops Acid (percent by weight)

| | Example # | | |
|---|---|---|---|
| | 14 | 15 | 16 |
| Citric Acid | 25.30 | 25.76 | 25.76 |
| Adipic Acid | 3.22 | 3.23 | 3.20 |
| Potassium Hydroxide, 45% | 53.90 | 54.78 | 54.80 |
| Glucopon 215UP, 62% | 11.80 | 10.40 | 10.40 |
| Hops acid, 30% | 2.87 | 2.92 | 2.92 |
| Ethanol, 99.5% | 2.91 | 2.91 | |
| Propylene glycol | | | 2.92 |
| pH | 8.80 | 8.88 | 9.13 |

Examples 17-18

In these examples, ethanol was used as solvent to dissolve both hops acid and citric acid in water (Table 6). However, this composition is considered flammable due to the presence of large amount of flammable solvent.

TABLE 6

Hops/Citric Acid Compositions
in Ethanol/Water (percent by weight)

| | Example # | |
|---|---|---|
| | 17 | 18 |
| Ethanol, 99.5% absolute | 35.08 | 32.79 |
| Citric acid, anhydrous | 39.50 | 40.82 |
| 30% Isoalpha Acid, Extract | 3.60 | 1.66 |
| D. Water | 21.82 | 24.53 |

Examples 19-20

In these samples, propylene glycol was added to mitigate the flammability of the compositions (Table 7). But propylene glycol is not a good solvent for citric acid, the active content is limited.

TABLE 7

Hops/Citric Acid Compositions in
Propylene Glycol/Ethanol/Water (percent by weight)

| | Example # | |
|---|---|---|
| | 19 | 20 |
| Ethanol, 99.5% absolute | 10.90 | 10.90 |
| Propylene glycol | 45.18 | 42.50 |
| Citric acid, anhydrous | 22.93 | 24.80 |
| 30% Isoalpha Acid, Extract | 2.09 | 1.13 |
| D. Water | 18.90 | 20.67 |

Example 21: MIC Determinations of Citric Acid/Hops Acid Compositions

In the following examples, the endpoint used to measure levels of antimicrobial activity is known as the Minimal Inhibitory Concentration, or MIC. This is the lowest concentration of a substance or substances which can achieve complete inhibition of growth.

Five milliliters of growth medium were inoculated with the appropriate test microbe and were incubated with shaking overnight. These overnight cultures (ON) were diluted 1:100 (100 µl of ON into 10 mL PBS). Corning 96-well microtiter plates were used and prepared by dispensing 252 µl of media into column 1 and 140 µl into columns 2-12. Next, 28 µl of the formulation was dispensed into column 1 to achieve a 1:10 dilution and the highest concentration of the composition to be tested. Column 1 was mixed by pipetting and twofold serial dilutions were carried out across the plate (140 µl of media+composition transferred each time). Column 12 was used as a composition-free control, therefore 140 µl of media+formulation from column 11 was removed to waste. Finally, 5 µl of bacteria was added to each well, yielding ~$5\times10^5$ cfu/ml. The 96 well plates were covered, sealed with parafilm and incubated at the appropriate temperature for 18-24 hours. The wells were scored as positive or negative for growth based on a visual examination for turbid wells, with turbidity being an indicator of growth. The lowest concentration of antimicrobial which completely inhibits growth (e.g., a clear well) is designated the Minimal Inhibitory Concentration.

TABLE 8

MIC Values

| Formulation | Citric Acid:Hops Acid | Test Microbe | Growth Media | MIC (ppm product) |
|---|---|---|---|---|
| Example 1 | 40:1 | L. plantarum | MRS Broth | 781 |
| Example 1 | 40:1 | S. aureus | M9YG | 781-3125 |
| | | | TSB | 391-1563 |
| Example 1 | 40:1 | B. subtilis | M9YG | 781-1563 |
| | | | TSB | 781-3125 |
| Example 2 | 80:1 | L. plantarum | MRS Broth | 781-1563 |
| Example 11 | 30:1 | L. plantarum | MRS Broth | 1722 |
| Example 14 | 30:1 | L. plantarum | MRS Broth | 2365 |
| Example 16 | 30:1 | L. plantarum | MRS Broth | 781-1563 |

What is claimed:

1. An aqueous antimicrobial composition containing a micro-emulsion, the micro-emulsion comprising:
    (i) at least one water soluble organic acid or its salt;
    (ii) at least one antimicrobial agent with limited water-solubility selected from the group consisting of hops acid, nisin, and a combination thereof; and
    (iii) at least one surfactant,
   wherein:
    (a) the water soluble organic acid or its salts comprises from 5 to 70% by total weight of the composition;
    (b) the antimicrobial agent comprises from 0.05 to 15% by total weight of the composition; and
    (c) the surfactant comprises from 0.1 to 30% by total weight of the composition.

2. The aqueous antimicrobial composition of claim 1, wherein the organic acid is selected from a mono- and polycarboxylic acid which have a pKa value related to a first dissociation stage of less than about 6, or its salt.

3. The aqueous antimicrobial composition of claim 1, wherein the organic acid is selected from the groups consisting of acetic acid, adipic acid, benzenesulfonic acid, benzoic acid, citric acid, gluconic acid, glutaric acid, hydroxyacetic acid, lactic acid, malic acid, methanesulphonic acid, oxalic acid, propionic acid, salicylic acid, succinic acid, tartaric acid, and mixtures thereof as well as their salts.

4. The aqueous antimicrobial composition of claim 1, wherein the antimicrobial agent comprises hops acid.

5. The aqueous antimicrobial composition of claim 1, further comprising:
   (iv) 0 to 20% by weight of co-surfactants or solvents based on total weight of the composition.

6. The aqueous antimicrobial composition of claim 1, further comprising a neutralizing agent.

7. The aqueous antimicrobial composition of claim 1, wherein the organic acid comprises citric acid or its salts.

8. The aqueous antimicrobial composition of claim 1, wherein the weight of the antimicrobial agent is from 0.1 to 10% by weight of the composition.

9. The aqueous antimicrobial composition of claim 1, wherein the weight of the surfactants is 1 to 20% by weight of the composition.

10. The aqueous antimicrobial composition of claim 1, wherein at least one surfactant is selected from the group consisting of polysorbates (polyoxyethylene sorbitan fatty acid esters), mono or dialkyl sulfosuccinates, alkyl polyglucosides and alkyl sulfates or combinations thereof.

11. The aqueous antimicrobial composition of claim 1, wherein at least one surfactant is selected from the group consisting of polyoxyethylene (20) sorbitan monooleate and alkyl polyglucosides.

12. The aqueous antimicrobial composition of claim 1, wherein the amount of the at least one organic acid is from 5 to 50% by total weight of the composition.

13. The aqueous antimicrobial composition of claim 7, wherein the amount of the at least one organic acid is from 15 to 60% by total weight of the composition.

14. The aqueous antimicrobial composition of claim 1, wherein the amount of the at least one organic acid is from 25-50% by total weight of the composition.

15. An aqueous antimicrobial composition containing a micro-emulsion, the micro-emulsion comprising:
   (i) citric acid or its salt;
   (ii) at least one antimicrobial agent with limited water-solubility selected from the group consisting of hops acid and nisin; and
   (iii) at least one surfactant,
   wherein:
      (a) the citric acid or its salt comprises 5 to 50% by total weight of the composition;
      (b) the antimicrobial agent comprises from 0.1 to 10% by total weight of the composition; and
      (c) the surfactant comprises from 1 to 30% by total weight of the composition.

16. The aqueous antimicrobial composition of claim 15 wherein the at least one antimicrobial agent comprises nisin.

17. The aqueous antimicrobial composition of claim 15 wherein the at least one antimicrobial agent comprises hops acid.

18. A method of controlling undesirable microorganism concentration in an aqueous solution employed in a fermentation process, the method comprising the steps of:
   (a) introducing a fermentable carbohydrate to an aqueous solution;
   (b) introducing at least one yeast to said solution; and
   (c) introducing the composition of claim 1 to the aqueous solution.

19. The method of claim 18 wherein the organic acid in the fermentation system is from 12500 ppm down to 100 ppm, and the amount of the antimicrobial agent with limited water-solubility in the fermentation system is from 0.5 ppm to 200 ppm.

20. The aqueous antimicrobial composition of claim 1, wherein the composition has a pH from about 2 to about 4.

21. The aqueous antimicrobial composition of claim 15, wherein the composition has a pH from about 2 to about 4.

22. The aqueous antimicrobial composition of claim 15, wherein the citric acid or its salt comprises from 15 to 50% by total weight of the composition.

* * * * *